United States Patent
Chiu (10) Patent No.: US 9,427,541 B2
(45) Date of Patent: Aug. 30, 2016

(54) SWITCHABLE ADAPTER FOR A SUCTION TUBE

(71) Applicant: VITALTEC CORPORATION, Taichung (TW)

(72) Inventor: Sheng-Yu Chiu, Taichung (TW)

(73) Assignee: VITALTEC CORPORATION, Taichung (TW)

( * ) Notice: Subject to any disclaimer, the term of this patent is extended or adjusted under 35 U.S.C. 154(b) by 308 days.

(21) Appl. No.: 14/265,940

(22) Filed: Apr. 30, 2014

(65) Prior Publication Data

US 2015/0314093 A1 Nov. 5, 2015

(51) Int. Cl.
*A61M 16/04* (2006.01)
*A61M 39/10* (2006.01)

(52) U.S. Cl.
CPC .......... *A61M 16/04* (2013.01); *A61M 16/0463* (2013.01); *A61M 39/10* (2013.01); *A61M 39/1055* (2013.01); *A61M 2039/1077* (2013.01)

(58) Field of Classification Search
CPC ........... A61M 16/04; A61M 16/0463; A61M 39/1055; A61M 39/10; A61M 2039/1077
USPC .................................................... 128/207.16
See application file for complete search history.

(56) References Cited

U.S. PATENT DOCUMENTS

| 5,181,508 | A | 1/1993 | Poole, Jr. | |
|---|---|---|---|---|
| 5,427,145 | A | 6/1995 | Grabenkort | |
| 6,612,304 | B1 * | 9/2003 | Cise ................. | A61M 16/0463 128/200.26 |
| 2004/0221852 | A1 | 11/2004 | Madsen | |
| 2010/0147310 | A1 * | 6/2010 | Brewer ............ | A61M 16/0463 128/207.14 |
| 2011/0155135 | A1 | 6/2011 | Chiu | |

FOREIGN PATENT DOCUMENTS

WO    WO 2004/011829    2/2004

* cited by examiner

*Primary Examiner* — Jason Flick
*Assistant Examiner* — Margaret Luarca
(74) *Attorney, Agent, or Firm* — Muncy, Geissler, Olds & Lowe, P.C.

(57) ABSTRACT

A switchable adapter for a suction tube has a manifold, a switching base rotatably connected to a pivot portion of the manifold, an air-tight component mounted between the pivot portion of the manifold and the switching base, and a cover mounted on an end of the pivot portion. The switching base has two connecting tubes. When the switching base pivots relative to the pivot portion of the manifold, the connecting tubes alternatively communicate with the manifold by rotation of the switching base. Thus, the switchable adapter is switched to allow the suction tube to suck sputa out of a trachea of a patient.

20 Claims, 11 Drawing Sheets

SWITCHABLE ADAPTER FOR A SUCTION TUBE

BACKGROUND OF THE INVENTION

1. Field of the Invention

The present invention relates to an adapter for a suction tube, especially to a switchable adapter for a suction tube.

2. Description of the Prior Art(s)

According to medical practice guidelines, when a patient is unable to swallow, to discharge sputa, or to breathe autonomously, or when respiratory disorders occur, an incision has to be made on an anterior portion of the neck of the patient in order to put a tracheotomy tube into a trachea of the patient through the incision. The tracheotomy tube is selectively connected to an oxygen supply apparatus, an open suction tube, or a closed suction tube via an adapter in order to assist the patient with breathing or to suck the sputa out of the trachea of the patient.

A conventional adapter for a suction tube, such as an ISOLATION VALVE FOR A CLOSED SUCTION DEVICE disclosed in U.S. patent publication No. 2011/0155135, has a body and a valve. The body has a communicating channel, a patient end connector, a breathing circuit connector and a suction tube connector. The communicating channel has a chamber and an opening. The patient end connector, the breathing circuit connector and the suction tube connector are radially formed on and protrude from the external surface of the communicating channel and communicate with the chamber of the communicating channel. The valve is rotatably connected to the body and has an isolation pipe and a control button. The isolation pipe is rotatably mounted in the chamber of the communicating channel via the opening and has a communicating hole, an inlet hole and a sucking hole. The control button is formed on the isolation pipe above the top of the communicating channel.

Another conventional adapter for a suction tube, such as a RESPIRATORY CARE ASSEMBLY disclosed in U.S. Pat. No. 6,612,304, comprises a manifold and an adapter. The manifold has an internal channel, multiple access ports, and a supporting component. The access ports of the manifold communicate with the internal channel and are respectively connected to the trachea of the patient and the oxygen supply apparatus. The supporting component has an opening communicating with the internal channel. The adapter is rotatably mounted on the supporting component and has two access ports respectively connected to the closed suction tube and the open suction tube. When the adapter is rotated, the adapter is switched, such that the two access ports of the adapter alternatively align with the opening of the supporting component to communicate with the internal channel of the manifold. While one of the access ports of the adapter communicates with the internal channel, the other one of the access ports of the adapter is separated from the internal channel.

However, when the adapter is rotated, exterior air may flow into the trachea of the patient through interstices between the adapter and the supporting component, putting the patient at the risk of infection. Moreover, since there are no alignment structures formed on the adapter and the supporting component, the medical personnel cannot be ensured whether the access port of the adapter has been aligned with the opening of the supporting component or not. Furthermore, the adapter has to be rotated 180 degrees to allow the other access port of the adapter to align with the opening of the supporting component, which is time-consuming and causes discomfort of the patient.

To overcome the shortcomings, the present invention provides a switchable adapter for a suction tube to mitigate or obviate the aforementioned problems.

SUMMARY OF THE INVENTION

The main objective of the present invention is to provide a switchable tube for a suction tube. The switchable adapter has a manifold, an air-tight component, a switching base, and a cover.

The manifold has a main tube, at least one branch tube, and a pivot portion. The main tube has an internal channel defined and extending between a front end of the main tube and a rear end of the main tube. The at least one branch tube is formed on and protrudes from the main tube, and communicates with the internal channel of the main tube. The pivot portion is attached to the rear end of the main tube and has a side recess and a mounting hole. The side recess is formed in an outer surface of the pivot portion. The mounting hole is formed through an inner sidewall defined in the side recess and communicates with the internal channel of the main tube.

The air-tight component is made of resilient material and has a main portion tightly fitted in the side recess of the pivot portion. The main portion of the air-tight component has a through hole aligning with and communicating with the internal channel of the main tube.

The switching base is pivotally connected to the pivot portion of the manifold and has a bottom panel, an arced sidewall, and two connecting tubes. The arced sidewall is formed on and protrudes up from the bottom panel. The pivot portion of the manifold is mounted in a pivot chamber surrounded by the arced sidewall of the switching base. The connecting tubes perpendicularly protrude from the arced sidewall. When the switching base pivots relative to the pivot portion of the manifold, the connecting tubes of the switching base alternatively align with the through hole of the air-tight component to communicate with the internal channel of the main tube of the manifold.

The cover is mounted on an end of the pivot portion of the manifold and is disposed opposite to the bottom panel of the switching panel.

An included angle defined between the two connecting tubes is only 30 to 90 degrees, such that rotating the switching base 30 is convenient and time-saving. Accordingly, chance of causing discomfort to the patient is greatly reduced. Furthermore, with the air-tight component tightly fitted in the side recess of the pivot portion, no exterior air would flow into the internal channel of the manifold through interstices between the pivot portion and the switching base, thereby preventing the patient from being infected.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
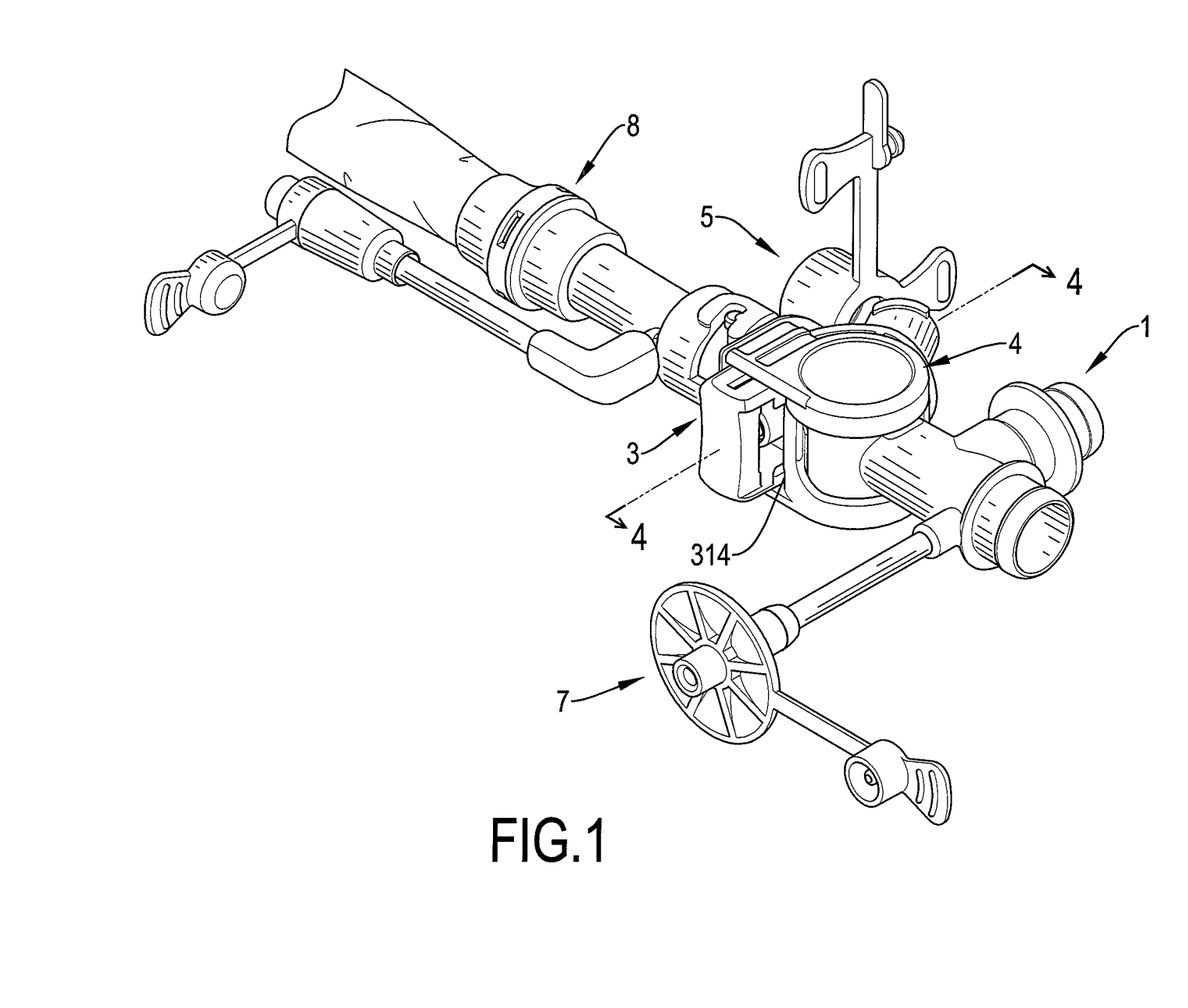
FIG. 1 is an operational perspective view of a switchable adapter for a suction tube in accordance with the present invention, shown connecting with a medicine feeding device and a closed suction tube.
Figure 2:
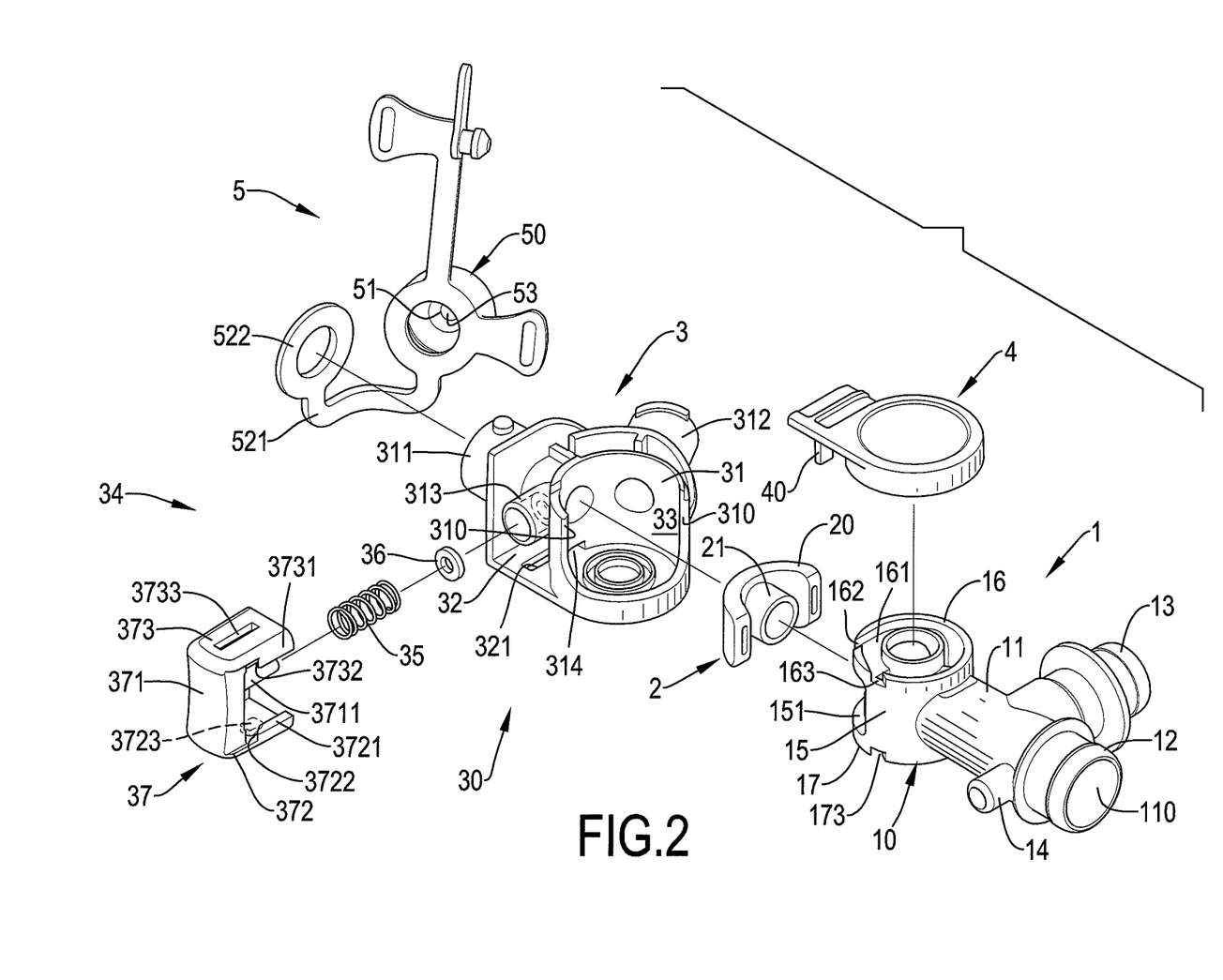
FIG. 2 is an exploded perspective view of the switchable adapter in FIG. 1.

With reference to FIGS. 1 and 2, a switchable adapter for a suction tube in accordance with the present invention comprises a manifold 1, an air-tight component 2, a switching base 30, a pressing assembly 34, a cover 4, and a cap set 5.

The manifold 1 has a main tube 11, at least one branch tube 12, 13, 14, and a pivot portion 10. The main tube 11 has a front end, a rear end, and an internal channel 110. The internal channel 110 is defined and extends between the front and the rear ends of the main tube 11. The at least one branch tube 12, 13, 14 is formed on and protrudes from the main tube 11, and communicates with the internal channel 110 of the main tube 11. Specifically, the manifold 1 has multiple branch tubes 12, 13, 14 including a trachea tube 12, an oxygen tube 13, and a medicine tube 14. The trachea tube 12 protrudes coaxially with the main tube 11 from the front end of the main tube 11. The oxygen tube 13 and the medicine tube 14 protrude perpendicularly from the main tube 11.

Figure 3:
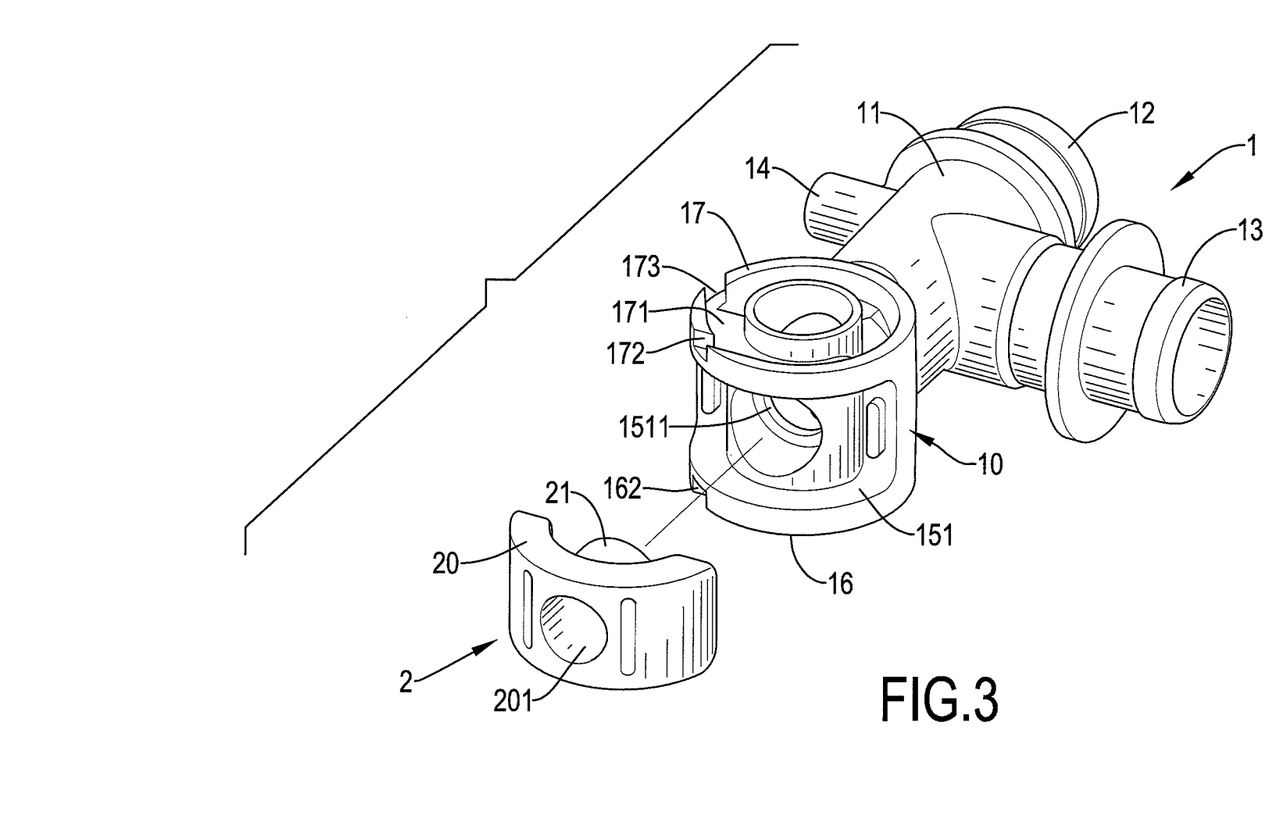
FIG. 3 is an exploded perspective view of a manifold and an air-tight component of the switchable adapter in FIG. 1.

With further reference to FIG. 3, the pivot portion 10 is attached to the rear end of the main tube 11, and has an outer surface 15, an upper end 16, a lower end 17, a side recess 151, an inner sidewall, a mounting hole 1511, an upper recess 161, an upper peripheral sidewall, a lower recess 171, and a lower peripheral sidewall. The outer surface 15 of the pivot portion 10 is attached to the rear end of the main tube 11. The side recess 151 is formed in the outer surface 15 of the pivot portion 10. The inner sidewall of the pivot portion 10 is defined in the side recess 151. The mounting hole 1511 is formed through the inner sidewall of the pivot portion 10 and communicates with the internal channel 110 of the main tube 11.

The upper recess 161 is formed in the upper end 16 of the pivot portion 10. The upper peripheral sidewall is defined around the upper recess 161 and has a first notch 162 and a second notch 163. The lower recess 171 is formed in the lower end 17 of the pivot portion 10. The lower peripheral sidewall is defined around the lower recess 171 and has a first notch 172 and a second notch 173. The first notch 172 of the lower peripheral sidewall corresponds in position to the first notch 162 of the upper peripheral sidewall. The second notch 173 of the lower peripheral sidewall corresponds in position to the second notch 163 of the upper peripheral sidewall.

The air-tight component 2 is made of resilient material, such as resilient plastic, and has a main portion 20 and a side tube 21. The main portion 20 may be arced, is tightly fitted in the side recess 151 of the pivot portion 10, and has a through hole 201 aligning with and communicating with the internal channel 110 of the main tube 11. Specifically, the main portion 20 is slightly larger than the side recess 151 of the pivot portion 10 in size, such that the main portion 20 is tightly fitted in the side recess 151 of the pivot portion 10. The side tube 21 protrudes from the main portion 20, is disposed around the through hole 201 of the main portion 20, protrudes in the mounting hole 1511 of the pivot portion 10, and communicates with the internal channel 110 of the main tube 11.

The switching base 30 is pivotally connected to the pivot portion 10 of the manifold 1 and has a bottom panel 32, an arced sidewall 31, a pivot chamber 33, at least one connecting tube 311, 312, and a mounting tube 313. The bottom panel 32 has a guiding slot 321 being elongated.

The arced sidewall 31 is formed on and protrudes up from the bottom panel 32, and has an inner arc surface, an outer arc surface, two side edges 310, and a mounting slot 314. The side edges 310 of the arced sidewall 31 are disposed apart from each other. The mounting slot 314 is formed through the arced sidewall 31, is disposed beside the bottom panel 32, and selectively corresponds in position to the first or the second notch 172, 173 of the lower peripheral sidewall of the pivot portion 10. The pivot chamber 33 is defined above the bottom panel 32, is surrounded by the arced sidewall 31, and receives the air-tight component 2 and the pivot portion 10 with the lower end 17 of the pivot portion 10 facing the bottom panel 32 and the main tube 11 protruding between the side edges 310 of the arced sidewall 31.

The at least one connecting tube 311, 312 perpendicularly protrudes from the outer arc surface of the arced sidewall 31 and communicates with the pivot chamber 33. Specifically, the switching base 30 has two connecting tubes 311, 312. When the switching base 30 pivots relative to the pivot portion 10 of the manifold 1 and about an axis perpendicular to the bottom panel 32 of the switching base 30, the side edges of the arced sidewall 31 alternatively move toward the main tube 11, and the two connecting tubes 311, 312 alternatively align with the through hole 201 of the air-tight component 2 to communicate with the internal channel 110 of the main tube 11. The two connecting tubes 311, 312 include a first connecting tube 311 and a second connecting tube 312. The first connecting tube 311 extends along a first axis. The second connecting tube 312 extends along a second axis. An included angle A defined between the first axis and the second axis is 30 to 90 degrees.

The mounting tube 313 perpendicularly protrudes from and communicates with the first connecting tube 311, corresponds in position to and extends parallel to the guiding slot 321 of the bottom panel 32, and has a distal end.

The pressing assembly 34 is mounted on the mounting tube 313 of the switching base 30, and has a pressing element 37 and a resilient element 35.

The pressing element 37 is disposed beside the distal end of the mounting tube 313 of the switching base 30 and has a force exertion portion 371, a guiding shaft 3711, and two guiding sidewalls 372, 373. The guiding shaft 3711 protrudes from the force exertion portion 371, is mounted in the mounting tube 313 of the switching base 30, and selectively protrudes into the first connecting tube 311. The guiding sidewalls 372, 373 separately protrude from the force exertion portion 371, and are oppositely disposed beside and parallel to the guiding shaft 3711. Each of the guiding sidewalls 372, 373 has an inner surface, an elongated edge, and a guiding wing 3721, 3731. The inner surface of the guiding sidewall 372, 373 faces the guiding shaft 3711. The elongated edge of the guiding sidewall 372, 373 corresponds in position to the arced sidewall 31 of the switching base 30. The guiding wing 3721, 3731 protrudes from the elongated edge of the guiding sidewall 372, 373, and has a rear end. The rear end of the guiding wing 3721, 3731 is disposed apart from the force exertion portion 371 to form a gap 3722, 3732 defined between the rear end of the guiding wing 3721, 3731 and the force exertion portion 371.

Figure 4:
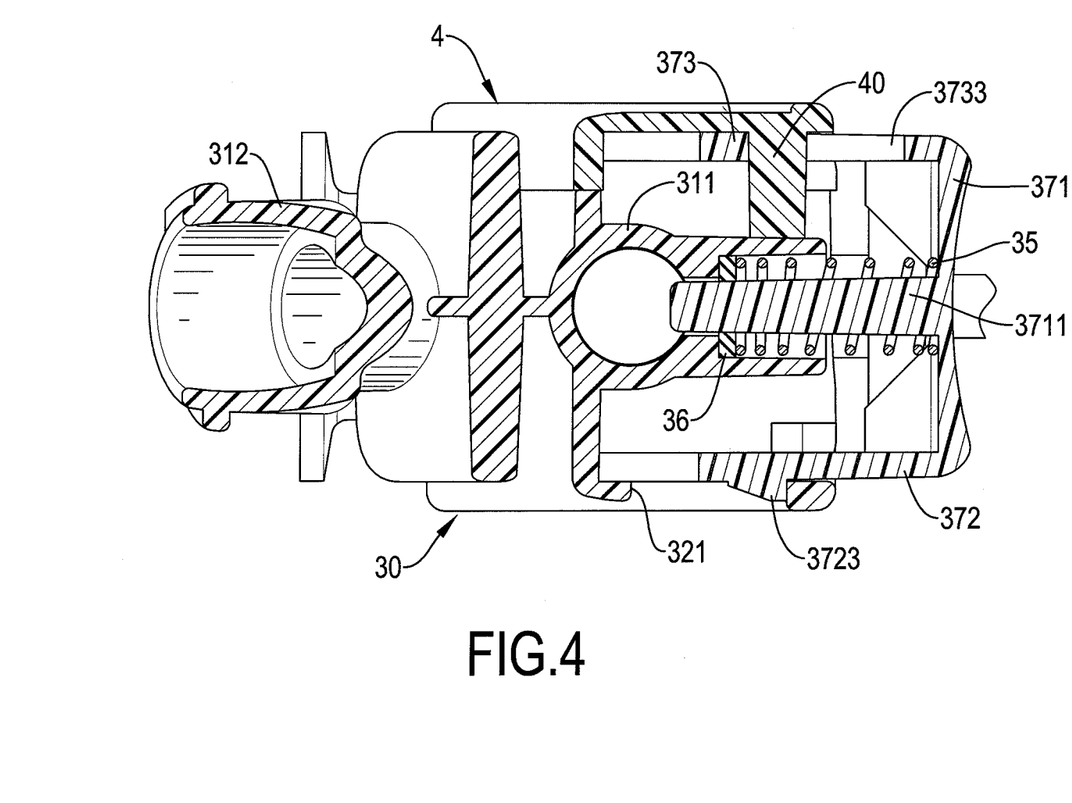
FIG. 4 is a cross-sectional side view of the switchable adapter in FIG. 1.
Figure 5:
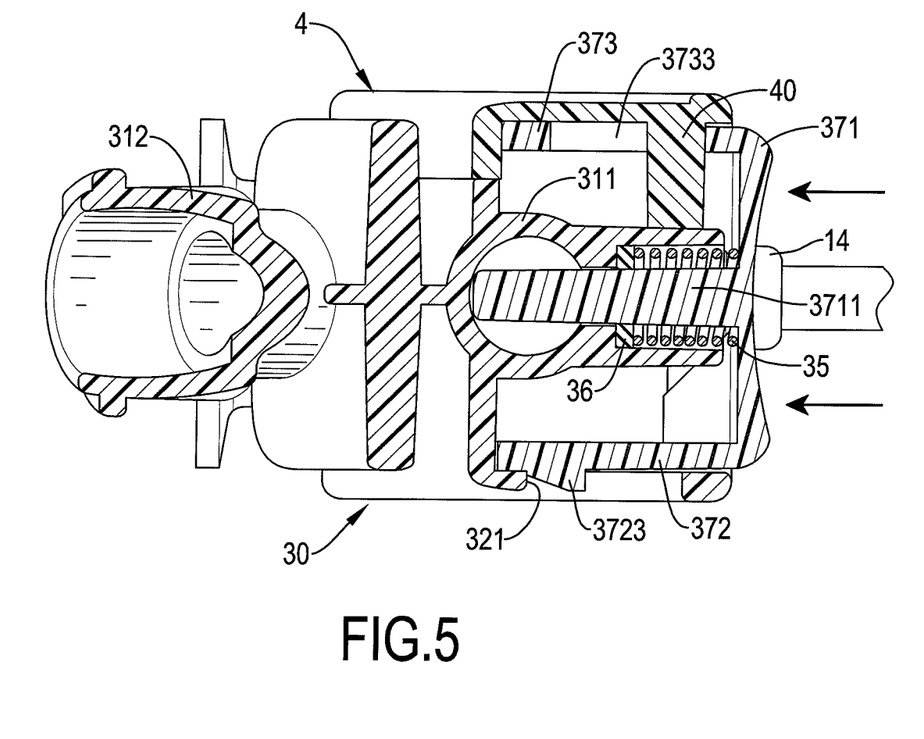
FIG. 5 is an operational cross-sectional side view of the switchable adapter in FIG. 1.

With further reference to FIGS. 4 and 5, specifically, the two guiding sidewalls 372, 373 include a first guiding sidewall 372 and a second guiding sidewall 373. The first guiding sidewall 372 further has a sliding protrusion 3723 formed on the inner surface of the first guiding sidewall 372 and protruding in the guiding slot 321 of the bottom panel 32. The guiding wing 3721 of the first guiding sidewall 372 is mounted through the mounting slot 314 of the arced sidewall 31, protrudes into the lower recess 171 of the pivot portion 10, and selectively engages in the first or the second notch 172, 173 of the lower peripheral sidewall of the pivot portion 10.

Figure 6:
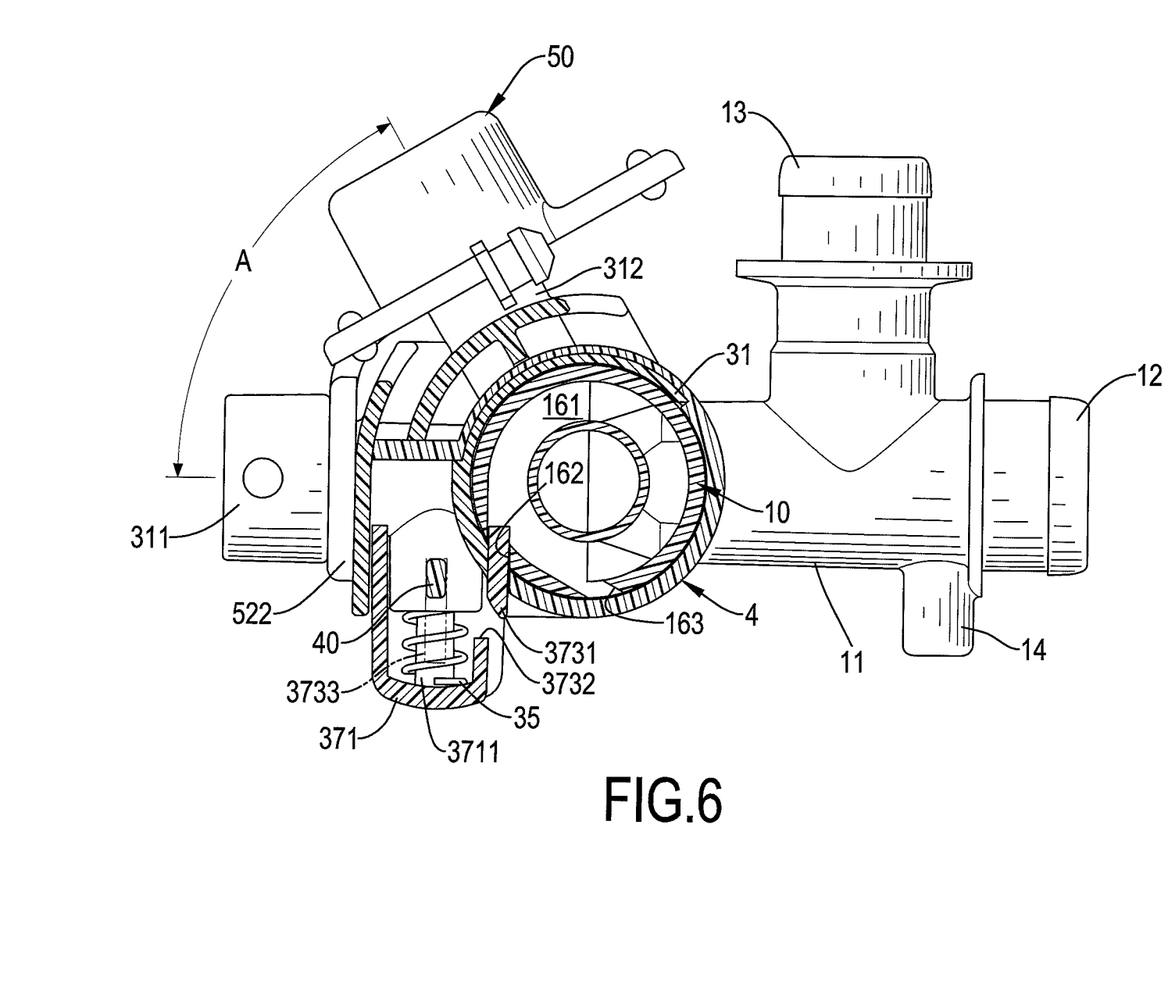
FIG. 6 is a cross-sectional top view of the switchable adapter in FIG. 1.

With further reference to FIG. 6, the second guiding sidewall 373 further has a sliding slot 3733. The sliding slot 3733 is elongated and is formed through the second guiding sidewall 373. The guiding wing 3731 of the second guiding sidewall 373 protrudes into the upper recess 161 of the pivot portion 10 and selectively engages in the first or the second notch 162, 163 of the upper peripheral sidewall of the pivot portion 10.

The resilient element 35 is mounted in the mounting tube 313 of the switching base 30, is mounted around the guiding shaft 3711 of the pressing element 37, and has two opposite ends respectively abutting the first connecting tube 311 and the force exertion portion 371 of the pressing element 37 to push the pressing element 37 to slide away from the switching base 30. Specifically, the resilient element 35 is a compression spring. With the resilient element 35 pushing the pressing element 37, the guiding wings 3721, 3731 securely engage in the first or the second notches 162, 163, 172, 173 of the pivot portion 10 of the manifold 1, such that the switching base 30 is held at a specific angular position relative to the pivot portion 10.

Preferably, the pressing assembly 34 further has a pad 36 mounted in the mounting tube 313 of the switching base 30. The two opposite ends of the resilient element 35 respectively abut the pad 36 and the force exertion portion 371 of the pressing element 37. The guiding shaft 3711 of the pressing element 37 is selectively mounted through the pad 36 to protrude into the first connecting tube 311.

The cover 4 is mounted on the upper end 16 of the pivot portion 10 of the manifold 1 and has an inner surface and a limiting protrusion 40. The limiting protrusion 40 protrudes from the inner surface of the cover 4 and protrudes in the sliding slot 3733 of the pressing element 37. With the limiting protrusion 40 of the cover 4 protruding in the sliding slot 3733 of the pressing element 37 and with the sliding protrusion 3723 of the pressing element 37 protruding in the guiding slot 321 of the bottom panel 32, a sliding range of the pressing element 37 is limited.

The cap set 5 is connected to the first connecting tube 311 of the switching base 30 and selectively caps a distal end of the second connecting tube 312 of the switching base 30. The cap set 5 includes a main cap 50, a sealing film 53, and a collar 522. The main cap 50 caps the distal end of the second connecting tube 312 and has a through hole 51 aligning with the second connecting tube 312. The sealing film 53 is mounted in the through hole 51 of the main cap 50 and has a peripheral edge partially attached to the main cap 50. Thus, the sealing film 53 selectively seals the through hole 51 of the main cap 50. The collar 522 is mounted around the first connecting tube 311 of the switching base 30 and is connected with the main cap 50 via a connecting strip 521.

As shown in FIG. 1, the trachea tube 12 is used to connect with a trachea of a patient, the oxygen tube 13 is used to connect with an oxygen supply system, and the medicine tube 14 is used to connect with a medicine feeding device 7.

With further reference to FIG. 6, when the first connecting tube 311 communicates with the internal channel 110 of the main tube 11, the guiding wings 3721, 3731 of the first and the second guiding sidewalls 372, 373 of the pressing element 37 engage in the first notches 172, 162 of the lower and the upper peripheral sidewalls of the pivot portion 10, and the second connecting tube 312 is separated from the internal channel 110 of the main tube 11. The first connecting tube 311 is used to connect with a closed suction tube 8. Thus, since the first connecting tube 311 communicates with the internal channel 110 of the main tube 11, the suction tube 8 can suck sputa out of the trachea of the patient.

Figure 7:
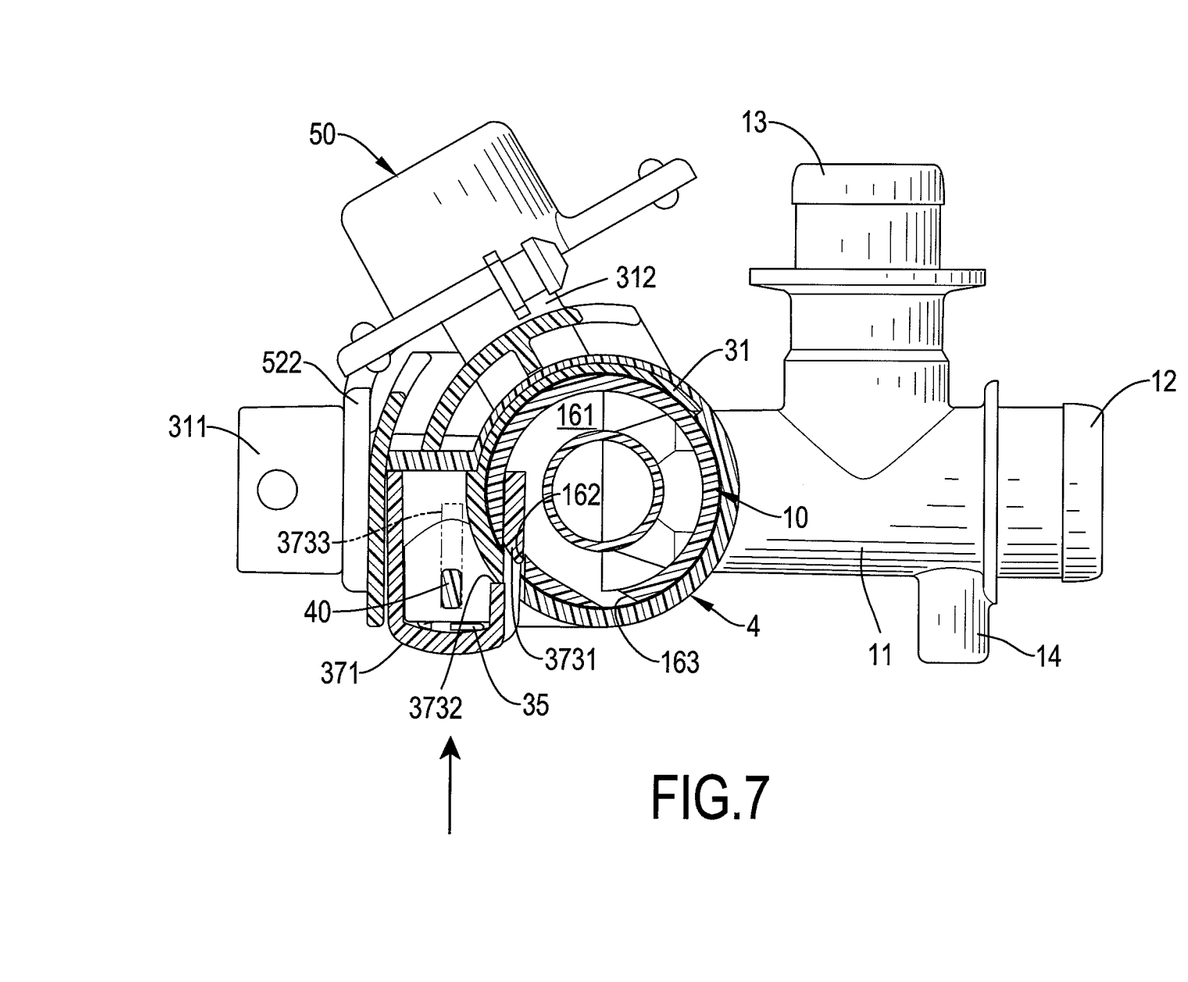
FIG. 7 is an operational cross-sectional top view of the switchable adapter in FIG. 1.

With further reference to FIG. 7, before switching the switching base 30 to allow the second connecting tube 312 to communicate with the internal channel 110 of the main tube 11, the pressing element 37 is pressed toward the first connecting tube 311, the resilient element 35 is compressed, and the guiding wings 3721, 3731 of the first and the second guiding sidewalls 372, 373 of the pressing element 37 disengage from the first notches 172, 162 of the lower and the upper peripheral sidewalls of the pivot portion 10. Thus, the switching base 30 is rotatable relative to the pivot portion 10 of the manifold 1.

When the switching base 30 is rotated, the lower peripheral sidewall and the upper peripheral side wall of the pivot portion 10 protrude in and engage respectively the gaps 3722, 3723 of the pressing element 37, such that the resilient element 35 cannot push the pressing element 37 backwardly.

Figure 8:
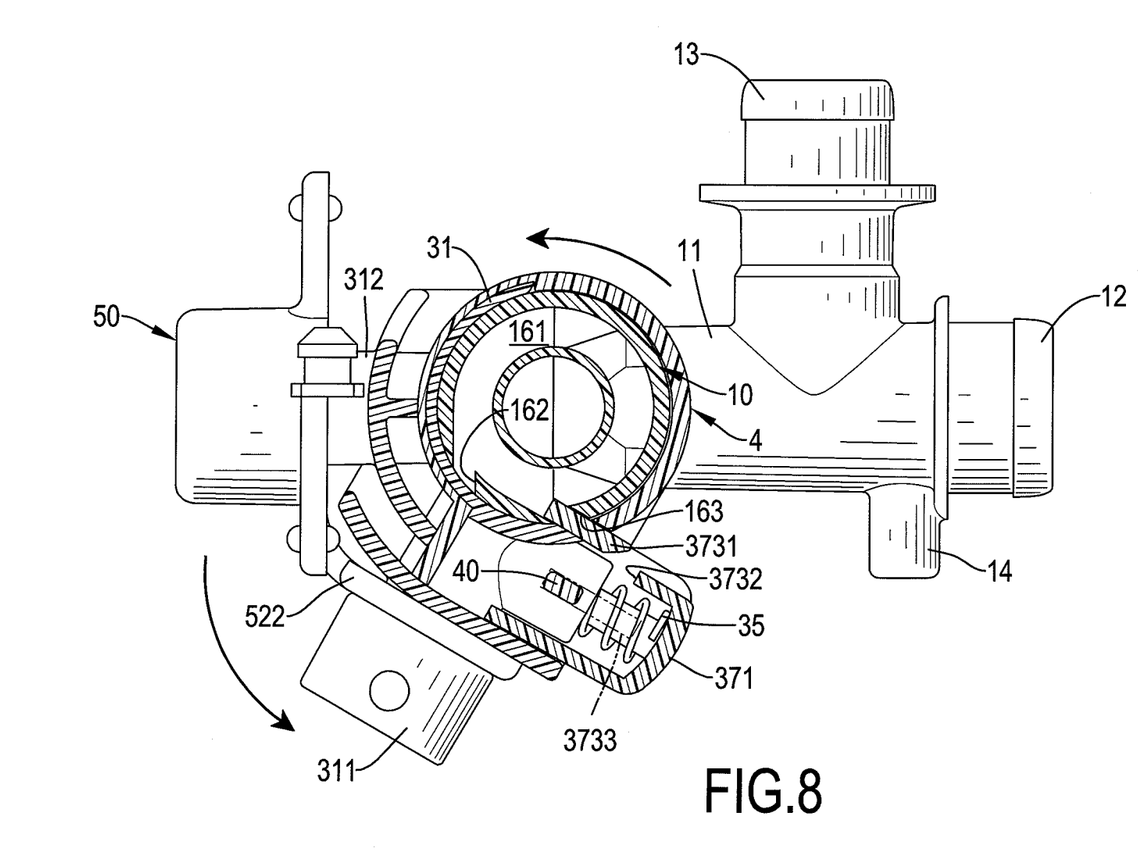
FIG. 8 is another operational cross-sectional top view of the switchable adapter in FIG. 1.

With further reference to FIG. 8, as the switching base 30 is rotated to allow the second connecting tube 312 to align with the through hole 201 of the air-tight component 2 and to communicate with the internal channel 110 of the manifold 1, the lower peripheral sidewall and the upper peripheral side wall of the pivot portion 10 respectively disengage from the gaps 3722, 3723 of the pressing element 37.

Thus, the resilient element 35 pushes the pressing element 37 backwardly, and the guiding wings 3721, 3731 of the first and the second guiding sidewalls 372, 373 of the pressing element 37 engage in the second notches 173, 163 of the lower and the upper peripheral sidewalls of the pivot portion 10.

With the guiding wings 3721, 3731 of the pressing element 37 selectively engage in the first or the second notches 172, 162, 173, 163 of the pivot portion 10, an operator can be sure that the first connecting tube 311 or the second connecting tube 312 has been communicating with the internal channel 110 of the manifold 1. Moreover, since the included angle A defined between the first connecting tube 311 and the second connecting tube 312 is only 30 to 90 degrees, rotating the switching base 30 is convenient and time-saving. Accordingly, the chance of causing discomfort to the patient is greatly reduced.

Furthermore, with the air-tight component 2 tightly fitted M the side recess 151 of the pivot portion 10, no exterior air would flow into the internal channel 110 of the manifold 1 through interstices between the pivot portion 10 and the switching base 30, thereby preventing the patient from being infected.

Figure 9:
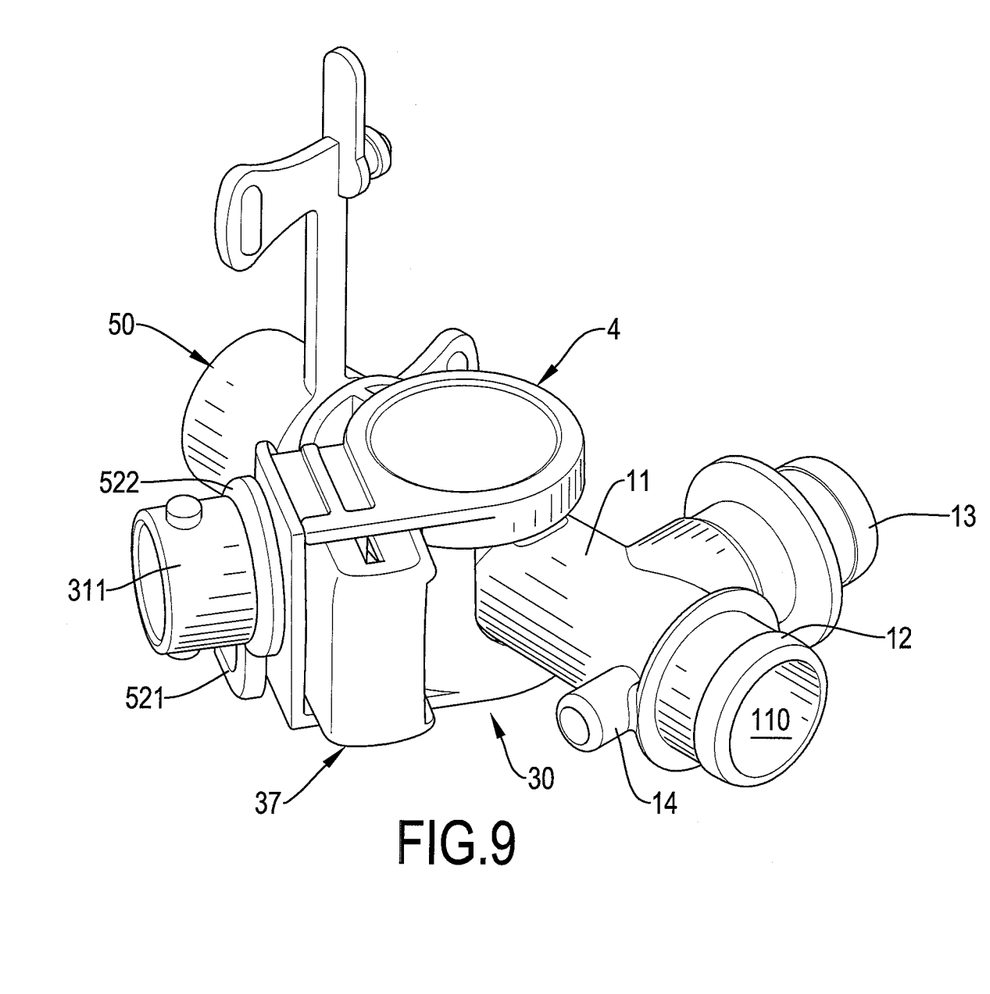
FIG. 9 is an operational perspective view of the switchable adapter in FIG. 1, showing a main cap caps a second connecting tube.

With further reference to FIG. 9, when the main cap 50 caps the distal end of the second connecting tube 312, the sealing film 53 separates the second connecting tube 312 and the internal channel 110 of the manifold 1 from an exterior environment. Thus, with the oxygen tube 13 connecting with the oxygen supply system, the switchable adapter of the present invention is used for supplying oxygen to the patient.

Figure 10:
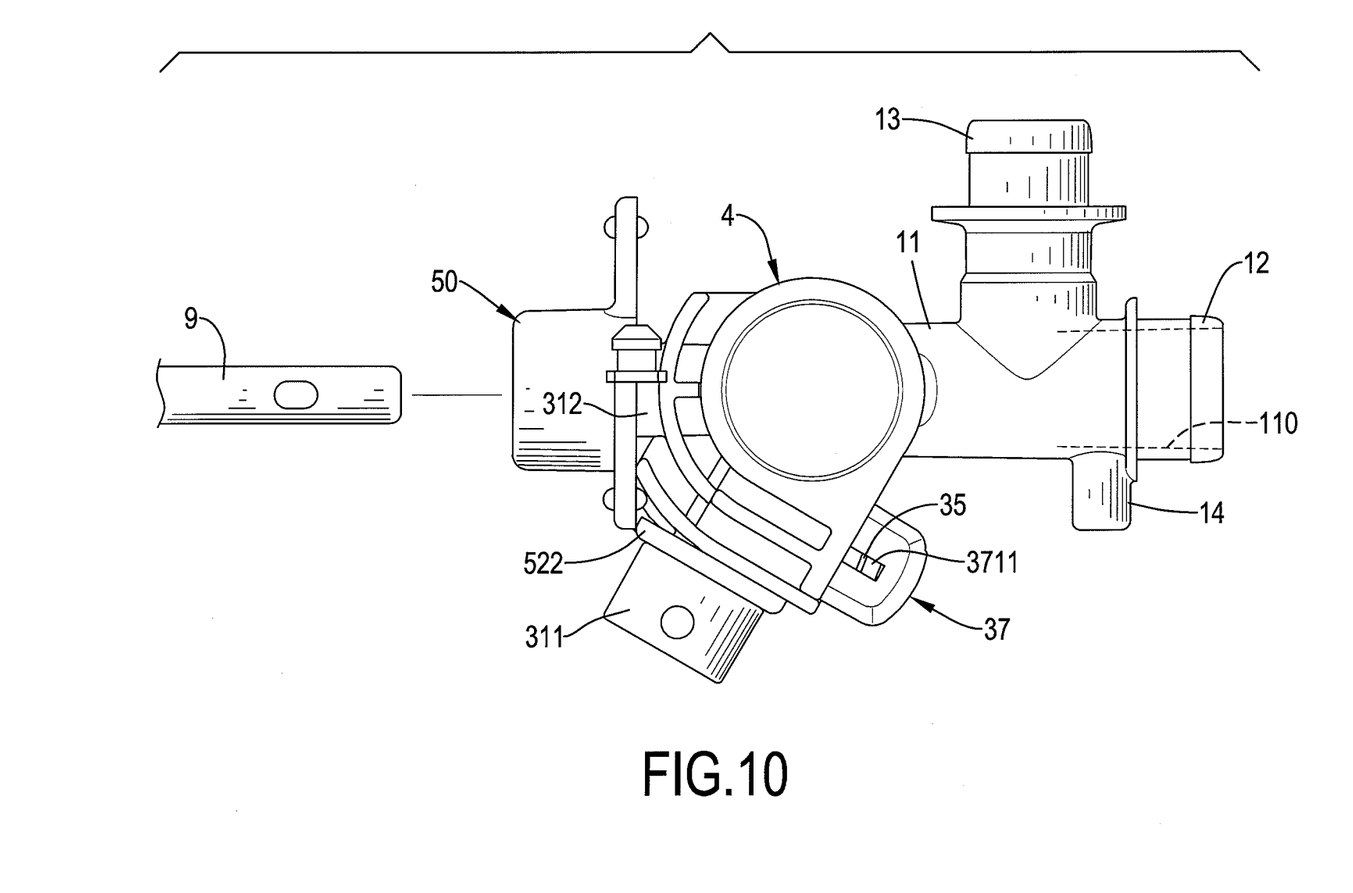
FIG. 10 is an operational top view of the switchable adapter in FIG. 1, showing the second connecting tube is used for receiving an open suction tube.

With further reference to FIG. 10, an open suction tube 9 can be further mounted into the through hole 51 of the main cap 50 to push and open the sealing film 53, and protrude into the second connecting tube 312 to suck the sputa out of the trachea of the patient.

Figure 11:
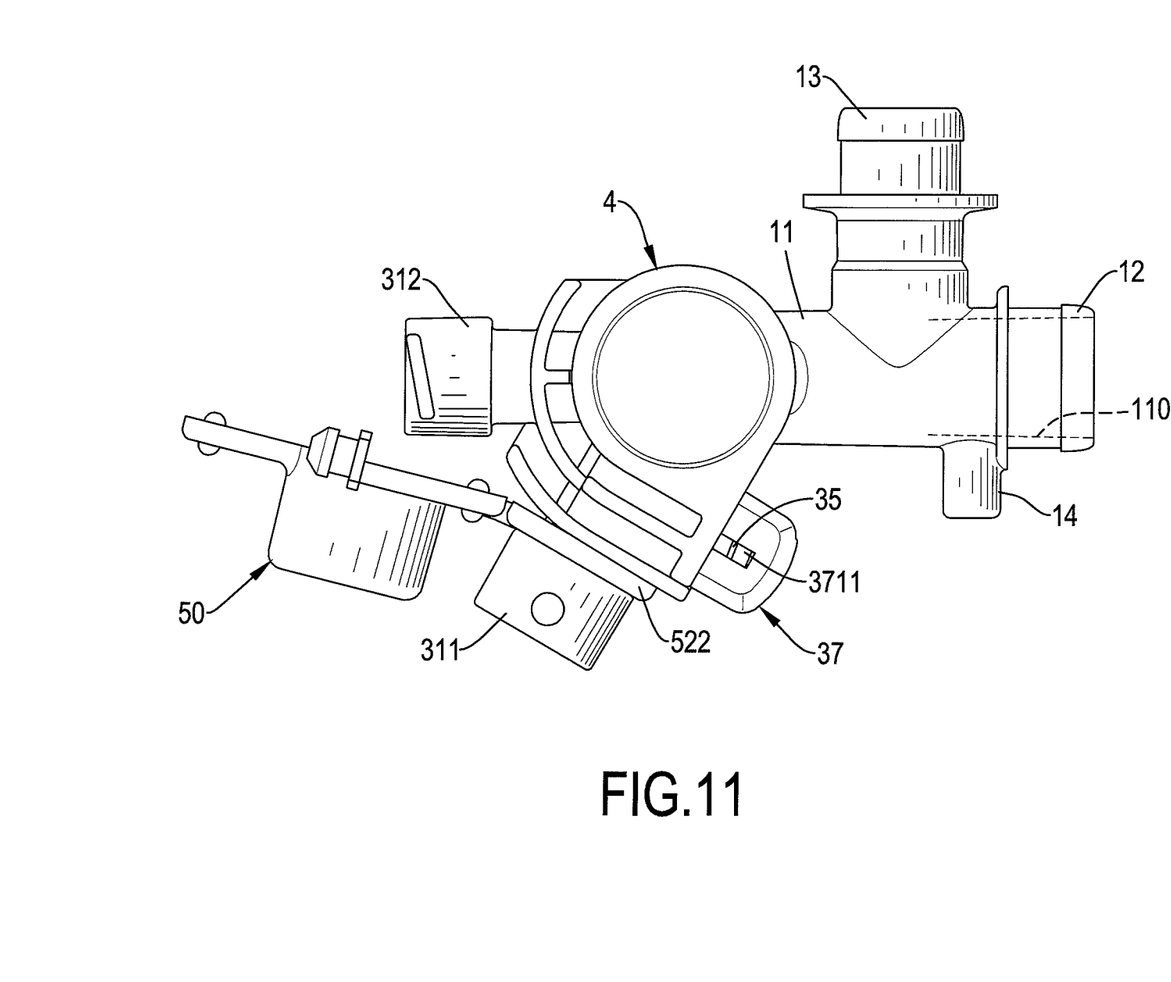
FIG. 11 is an operational top view of the switchable adapter in FIG. 1, showing the main cap is removed from the second connecting tube.

With further reference to FIG. 11, when the main cap 50 is removed from the second connecting tube 312, an endoscope can be directly inserted into the second connecting tube 312 and the trachea of the patient to examine the trachea of the patient.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A switchable adapter for a suction tube comprising:
    a manifold having
        a main tube having an internal channel defined and extending between a front end of the main tube and a rear end of the main tube;
        at least one branch tube formed on and protruding from the main tube, and communicating with the internal channel of the main tube; and
        a pivot portion attached to the rear end of the main tube, and having an outer surface attached to the rear end of the main tube;
        an upper end;
        a lower end;
        a side recess formed in the outer surface of the pivot portion;
        an inner sidewall defined in the side recess; and
        a mounting hole formed through the inner sidewall of the pivot portion and communicating with the internal channel of the main tube;
    an air-tight component made of resilient material and having a main portion fitted in the side recess of the pivot portion, and having a through hole aligning with and communicating with the internal channel of the main tube;
    a switching base rotatably connected to the pivot portion of the manifold and having a bottom panel;
    an arced sidewall formed on and protruding up from the bottom panel, and having an inner arc surface, an outer arc surface, and two side edges disposed apart from each other;
    a pivot chamber defined above the bottom panel, surrounded by the arced sidewall, and receiving the air-tight component and the pivot portion with the lower end of the pivot portion facing the bottom panel and the main tube protruding between the side edges of the arced sidewall; and
    two connecting tubes including a first connecting tube and a second connecting tube, and the connecting tubes perpendicularly protruding from the outer surface of the arced sidewall; and
    wherein when the switching base pivots relative to the pivot portion of the manifold, the side edges of the arced sidewall alternatively move toward the main tube, and the connecting tubes of the switching base alternatively align with the through hole of the air-tight component to communicate with the internal channel of the main tube of the manifold.

2. The switchable adapter as claimed in claim 1, wherein the pivot portion of the manifold further has
    an upper recess formed in the upper end of the pivot portion;
    an upper peripheral sidewall defined around the upper recess, and having a first notch and a second notch;
    a lower recess formed in the lower end of the pivot portion; and
    a lower peripheral sidewall defined around the lower recess and having a first notch and a second notch;
the arced sidewall of the switching base further has a mounting slot formed through the arced sidewall, disposed beside the bottom panel, and selectively corresponding in position to the first or the second notch of the lower peripheral sidewall of the pivot portion;
the switching base further has a mounting tube perpendicularly protruding from the first connecting tube and having a distal end; and
the switchable adapter further comprises a pressing assembly mounted on the mounting tube of the switching base and having
    a pressing element disposed beside the distal end of the mounting tube of the switching base and having
        a force exertion portion; and
        two guiding sidewalls separately protruding from the force exertion portion, and the two guiding sidewalls including
            a first guiding sidewall having
                an elongated edge corresponding in position to the arced sidewall of the switching base; and
                a guiding wing protruding from the elongated edge of the first guiding sidewall and having a rear end disposed apart from the force exertion portion to form a gap defined between the rear end of the guiding wing of the first guiding sidewall and the force exertion portion; and
            a second guiding sidewall having
                an elongated edge corresponding in position to the arced sidewall of the switching base;
                a guiding wing protruding from the elongated edge of the first guiding sidewall and having a rear end disposed apart from the force exertion portion to form a gap defined between the rear end of the guiding wing of the second guiding sidewall and the force exertion portion; and
                a sliding slot being elongated and formed through the second guiding sidewall; and
    a resilient element mounted in the mounting tube of the switching base and having two opposite ends respectively abutting the first connecting tube and the force exertion portion of the pressing element to push the pressing element to slide away from the switching base; and the cover has an inner surface and a limiting protrusion protruding from the inner surface of the cover and protruding in the sliding slot of the pressing element;
wherein the guiding wing of the first guiding sidewall is mounted through the mounting slot of the arced sidewall, protrudes into the lower recess of the pivot portion, and selectively engages in the first or the second notch of the lower peripheral sidewall of the pivot portion; and
the guiding wing of the second guiding sidewall protrudes into the upper recess of the pivot portion and selectively engages in the first or the second notch of the upper peripheral sidewall of the pivot portion.

3. The switchable adapter as claimed in claim 2, wherein
the bottom panel of the switching base has a guiding slot corresponding in position to and extending parallel to the mounting tube; and
the first guiding sidewall of the pressing element further has a sliding protrusion formed on an inner surface of the first guiding sidewall and protruding in the guiding slot of the bottom panel.

4. The switchable adapter as claimed in claim 3, wherein
the pressing element further has a guiding shaft protruding from the force exertion portion of the pressing element and mounted in the mounting tube of the switching base; and
the resilient element is mounted around the guiding shaft of the pressing element.

5. The switchable adapter as claimed in claim 2, wherein
the mounting tube of the switching base communicates with the first connecting tube of the switching base;
the pressing assembly further has a pad mounted in the mounting tube of the switching base;
the two opposite ends of the resilient element respectively abut the pad and the force exertion portion of the pressing element; and
the guiding shaft of the pressing element is selectively mounted through the pad to protrude into the first connecting tube of the switching base.

6. The switchable adapter as claimed in claim 2, wherein
the first connecting tube of the switching base extends along a first axis;
the second connecting tube of the switching base extends along a second axis; and
an included angle defined between the first axis and the second axis is 30 to 90 degrees.

7. The switchable adapter as claimed in claim 3, wherein
the first connecting tube of the switching base extends along a first axis;
the second connecting tube of the switching base extends along a second axis; and
an included angle defined between the first axis and the second axis is 30 to 90 degrees.

8. The switchable adapter as claimed in claim 4, wherein
the first connecting tube of the switching base extends along a first axis;
the second connecting tube of the switching base extends along a second axis; and
an included angle defined between the first axis and the second axis is 30 to 90 degrees.

9. The switchable adapter as claimed in claim 5, wherein
the first connecting tube of the switching base extends along a first axis;
the second connecting tube of the switching base extends along a second axis; and
an included angle defined between the first axis and the second axis is 30 to 90 degrees.

10. The switchable adapter as claimed in claim 6 further comprising a cap set selectively capping a distal end of the second connecting tube of the switching base, and the cap set including
a main cap capping the distal end of the second connecting tube and having a through hole aligning with the second connecting tube; and
a sealing film mounted in the through hole of the main cap and having a peripheral edge partially attached to the main cap, such that the sealing film selectively seals the through hole of the main cap.

11. The switchable adapter as claimed in claim 7 further comprising a cap set selectively capping a distal end of the second connecting tube of the switching base, and the cap set including
a main cap capping the distal end of the second connecting tube and having a through hole aligning with the second connecting tube; and
a sealing film mounted in the through hole of the main cap and having a peripheral edge partially attached to the main cap, such that the sealing film selectively seals the through hole of the main cap.

12. The switchable adapter as claimed in claim 8 further comprising a cap set selectively capping a distal end of the second connecting tube of the switching base, and the cap set including
a main cap capping the distal end of the second connecting tube and having a through hole aligning with the second connecting tube; and
a sealing film mounted in the through hole of the main cap and having a peripheral edge partially attached to the main cap, such that the sealing film selectively seals the through hole of the main cap.

13. The switchable adapter as claimed in claim 9 further comprising a cap set selectively capping a distal end of the second connecting tube of the switching base, and the cap set including
a main cap capping the distal end of the second connecting tube and having a through hole aligning with the second connecting tube; and
a sealing film mounted in the through hole of the main cap and having a peripheral edge partially attached to the main cap, such that the sealing film selectively seals the through hole of the main cap.

14. The switchable adapter as claimed in claim 10, wherein the cap set further has a collar mounted around the first connecting tube of the switching base and connected with the main cap via a connecting strip.

15. The switchable adapter as claimed in claim 11, wherein the cap set further has a collar mounted around the first connecting tube of the switching base and connected with the main cap via a connecting strip.

16. The switchable adapter as claimed in claim 12, wherein the cap set further has a collar mounted around the first connecting tube of the switching base and connected with the main cap via a connecting strip.

17. The switchable adapter as claimed in claim 13, wherein the cap set further has a collar mounted around the first connecting tube of the switching base and connected with the main cap via a connecting strip.

18. The switchable adapter as claimed in claim 14, wherein the air-tight component further has a side tube protruding from the main portion, disposed around the through hole of the main portion, protruding in the mounting hole of the pivot portion, and communicating with the internal channel of the main tube.

19. The switchable adapter as claimed in claim 15, wherein the air-tight component further has a side tube protruding from the main portion, disposed around the through hole of the main portion, protruding in the mounting hole of the pivot portion, and communicating with the internal channel of the main tube.

20. The switchable adapter as claimed in claim 17, wherein the air-tight component further has a side tube protruding from the main portion, disposed around the through hole of the main portion, protruding in the mounting hole of the pivot portion, and communicating with the internal channel of the main tube.

* * * * *